United States Patent
Fredric

(10) Patent No.: US 11,313,621 B2
(45) Date of Patent: Apr. 26, 2022

(54) MOISTURE MEASUREMENT OF TIMBER

(71) Applicant: Malcolm Fredric, Porirua (NZ)

(72) Inventor: Malcolm Fredric, Porirua (NZ)

(73) Assignee: WINDSOR ENGINEERING GROUP LIMITED, Porirua (NZ)

(*) Notice: Subject to any disclaimer, the term of this patent is extended or adjusted under 35 U.S.C. 154(b) by 99 days.

(21) Appl. No.: 16/754,949

(22) PCT Filed: Oct. 12, 2018

(86) PCT No.: PCT/NZ2018/050141
§ 371 (c)(1),
(2) Date: Apr. 9, 2020

(87) PCT Pub. No.: WO2019/074382
PCT Pub. Date: Apr. 18, 2019

(65) Prior Publication Data
US 2021/0010752 A1    Jan. 14, 2021

(30) Foreign Application Priority Data
Oct. 13, 2017   (NZ) ........................................ 736392

(51) Int. Cl.
F26B 25/22   (2006.01)
G01N 22/04   (2006.01)
G01N 33/46   (2006.01)

(52) U.S. Cl.
CPC .............. *F26B 25/22* (2013.01); *G01N 22/04* (2013.01); *G01N 33/46* (2013.01); *F26B 2210/16* (2013.01)

(58) Field of Classification Search
CPC ..... F26B 25/22; F26B 2210/16; G01N 22/04; G01N 33/46
(Continued)

(56) References Cited

U.S. PATENT DOCUMENTS 1,784,727 A * 12/1930 Harris ....................... F26B 9/06
                                                                 34/72
3,574,949 A *  4/1971 Farnsworth ............. F26B 23/06
                                                                 34/407
(Continued)

FOREIGN PATENT DOCUMENTS

| WO | WO 2002/014848 A1 | 2/2002 | |
| WO | WO 2015/058027 A1 | 4/2015 | |
| WO | WO-2019074382 A1 * | 4/2019 | ............. G01N 33/46 |

OTHER PUBLICATIONS

International Search Report issued in International Application No. PCT/NZ2018/050141, dated Jan. 22, 2019.
(Continued)

*Primary Examiner* — Stephen M Gravini
(74) *Attorney, Agent, or Firm* — Charles C. Achkar; Ostrolenk Faber LLP.

(57) ABSTRACT

A kiln moisture measurement method and system is provided for measuring the moisture level of a charge of timber in a timber drying kiln. The method includes steps of: transmitting electromagnetic radiation from a transmitter; receiving the electromagnetic radiation at a receiver; wherein the transmitter and receiver are configured such that the electromagnetic radiation passes through at least part of the charge of timber. An electronic data processor determines the gain of the electromagnetic radiation by comparing the intensities of the transmitted and received electromagnetic radiation; and subsequently determines a moisture level of the charge based on the gain of the electromagnetic radiation.

64 Claims, 10 Drawing Sheets

(58) Field of Classification Search
USPC .......................................................... 34/466
See application file for complete search history.

(56) References Cited

U.S. PATENT DOCUMENTS

| | | | | |
|---|---|---|---|---|
| 4,893,415 | A * | 1/1990 | Moldrup | F26B 23/005 34/406 |
| 5,086,279 | A | 2/1992 | Wochnowski et al. | |
| 6,675,495 | B2 * | 1/2004 | Dedieu | F26B 3/343 210/748.07 |
| 6,989,678 | B2 * | 1/2006 | Venter | G01N 27/223 324/521 |
| 7,748,137 | B2 * | 7/2010 | Wang | F26B 3/28 34/396 |
| 7,993,709 | B2 * | 8/2011 | Brunet | C10L 9/083 427/440 |
| 8,578,625 | B2 * | 11/2013 | Franich | F26B 21/06 34/367 |
| 10,533,799 | B2 * | 1/2020 | Triglia, Jr. | F26B 13/008 |
| 10,757,960 | B2 * | 9/2020 | Tanaka | B01J 19/10 |
| 2003/0062908 | A1 | 4/2003 | Venter et al. | |
| 2003/0146767 | A1 | 8/2003 | Steele et al. | |
| 2009/0113752 | A1 * | 5/2009 | Weir | F26B 21/06 34/282 |
| 2021/0010752 | A1 * | 1/2021 | Fredric | F26B 25/22 |
| 2021/0260788 | A1 * | 8/2021 | Jeong | B27K 3/34 |

OTHER PUBLICATIONS

Written Opinion of the International Searching Authority issued in International Application No. PCT/NZ2018/050141, dated Jan. 22, 2019.

* cited by examiner

MOISTURE MEASUREMENT OF TIMBER

FIELD OF THE DISCLOSURE

This disclosure relates to a method and system for measuring the moisture content of timber using electromagnetic radiation, and more specifically to a kiln moisture measurement system and kiln moisture measurement method for measuring the moisture content of timber in a drying kiln using radio-frequency radiation.

BACKGROUND TO THE DISCLOSURE

Any discussion of the prior art throughout the specification should in no way be considered as an admission that such prior art is widely known or forms part of common general knowledge in the field.

Drying kilns are commonly used to remove moisture from a charge of sawn timber. Three common types of timber drying kiln are batch kilns, progressive kilns and continuous drying kilns.

The most common drying kiln is the batch kiln, which is a sealed chamber where heating, airflow, and humidity can be controlled. The charge is loaded into the chamber, which is then heated to provide drying conditions. During the drying process, the charge remains stationary. The chamber is then opened and the charge is removed. Drying kilns in the form of batch kilns typically have one door through which the charge enters, and the same or another door through which the charge exits the chamber.

Progressive kilns typically consist of one or more independently heated, sealed chambers. Therefore, progressive kilns are slightly modified batch kilns and operate like a batch kiln. The chambers can be placed end to end and they may have doors at each end. The charge is placed into the first chamber, which is sealed and brought up to the required pre-drying conditions. The chamber is then opened, and the charge is moved into the next chamber, which is then sealed and brought up to the required drying conditions. Next, the charge is moved into the conditioning chamber, which is sealed and brought up to the required conditioning conditions. Each chamber is independently powered and the thermal energy is vented into the environment after each stage. The amount by which the charge moves through the chambers is dependent on the size of the chamber and the batch size.

Continuous kilns incorporate multiple sub chambers or phases all in one extended chamber, with each sub chamber subjecting the timber to different conditions, as the timber moves through the extended chamber. For example there may be sub chambers for pre-heating, drying, cooling, and conditioning, all in one extended chamber.

Dual path continuous kilns typically consist of two tracks or paths of timber on carts travelling in opposite directions through the chamber. Green timber is introduced at each end of the chamber on opposing paths. There is a heating zone in the middle of the chamber and a heat transfer zone at each end. In the heat transfer zones, heat from the dried timber on one path is transferred by fans to the green timber on the other path, in order to improve the efficiency of the drying process. Each of the two rows of carts may move continuously or in increments, and the chamber has no sealed doors.

An example of a continuous kiln is described in international patent application WO2015/093986 (PCT/NZ2014/050008) filed on 6 Nov. 2014, the entire contents of which are hereby incorporated by reference.

Efficient use of timber drying kilns requires the ability to measure the moisture content of the timber being dried, with an aim being to dry the timber to a desired moisture content. It is desirable to avoid overdrying of the timber, and also desirable to avoid having to perform a further drying operation on timber that has been insufficiently dried in the first instance.

To this end, efficient operation of a timber drying kiln requires the assessment of the moisture content of a cross section of timber. The ability to determine endpoint moisture contents in the kiln, e.g. during the drying operation of the kiln, allows more uniform product quality and decreased drying costs as there are reduced instances of overdrying or the need to repeat a drying operation. Opening the door of a kiln where the kiln is still warm causes a loss of thermal energy, and if it is determined that the charge requires further drying, the kiln will need to be reheated to restore the drying conditions, requiring additional energy.

In situ methods of determining the moisture content of drying materials in a kiln are known. For example, U.S. Pat. No. 6,463,794 describes a system for determining the moisture content of plant matter by measuring the temperature, humidity and flow rate of forced air entering and exiting a heating area. Another method of measuring moisture content in timber is described in U.S. Pat. No. 6,989,678, which describes a system for determining the moisture content of timber in a kiln by insertion of electrodes and/or capacitance plates into spaces between layers in a stack of timber, wherein the capacitive and/or resistive parameters are used to determine a value corresponding to a moisture content.

However, current endpoint moisture measurement systems using electrodes and/or capacitance plates are difficult to handle, especially in a continuous environment, since they need to be loaded into each stack before entry into the kiln, and removed after exit.

Charges of timber may be higher than the height of an operator (often over 2 meters high), and sometimes the charge may be assembled sub-adequately; for example, the charge may be leaning to one side, or may be unsteady (e.g. the charge may wobble or become unstable during movement). Thus, charges of timber pose a health and safety risk to operators as there is a risk that the charge may topple. Requiring operators to approach a charge of timber to install moisture reader electrodes or plates into the charge therefore presents a hazard. Further, moisture readers may not be able to be installed until the charge has reached, or is already inside, a drying kiln. Requiring operators to enter a kiln to install moisture readers into a charge of timber located in a kiln also presents health and safety risks, as wood drying kilns are hazardous for numerous reasons, including being a high temperature environment and/or an enclosed space which may harbour noxious fumes or gases.

It would be desirable to provide a kiln moisture measurement system which did not require an operator to enter the kiln.

A further problem is that in particularly cold environments, moisture reader plates may freeze to the charge of timber if the charge cools substantially. This creates a health and safety risk, as well as being inconvenient, for the operators who will need to detach the moisture reader probes.

Charges of timber have different properties (e.g. relative permittivity, density, moisture content) at different locations. In particular the moisture content of timber in the charge or stack of timber can vary significantly in different parts of the charge. This means that multiple measurements often need to be taken at different parts of a charge of timber in order to determine a representative or average moisture content or to ensure that the entirety of the charge is sufficiently dry.

If moisture measuring systems are not easy to use they will simply not be used by operators, and the advantages and economic gains enabled by in situ moisture measuring processes will not be realised in practice.

Object of the Disclosure

It is an object of the disclosure to provide a kiln moisture measurement system and kiln moisture measurement method for measuring the moisture content of timber which mitigates one or more of the aforementioned problems, or to at least provide the public with a useful choice.

SUMMARY OF THE DISCLOSURE

We have found that it is possible to provide a kiln timber moisture measurement system comprising at least one transmitting and receiving antennae which can be mounted in a kiln and can transmit radio frequency electromagnetic signals through a charge of drying timber, during operation of the kiln (that is, when the kiln is drying the timber) and that the measured gain of the received signal correlates with the moisture content of the charge.

In one aspect, there is provided a kiln moisture measurement method for measuring the moisture level of a charge of timber in a timber drying kiln, including steps of: transmitting electromagnetic radiation from a transmitter; receiving the electromagnetic radiation at a receiver; wherein the transmitter and receiver are configured to be on opposed parts of at least part of the charge of timber such that the electromagnetic radiation passes through the at least part of the charge of timber; determining, using an electronic data processor, the gain of the electromagnetic radiation by comparing the intensities (e.g. amplitudes) of the transmitted and received electromagnetic radiation; and determining a moisture level of the charge based on the gain of the electromagnetic radiation.

Preferably, the charge of timber has primary dimension (e.g. width, length or height), and the transmitter and receiver are located such that the received electromagnetic radiation is transmitted through the primary dimension of the charge.

The transmitted electromagnetic radiation has a frequency in the range of 150 MHz to 4 GHz, preferably in the UHF or VHF band (that is, 150 MHz to 1 GHz), more preferably in the range of about 280 MHz to 500 MHz, and most preferably in the range of about 290 MHz to about 310 MHz.

Preferably, the transmitter and receiver are located on opposed side walls of the kiln, and on opposed sides of the charge of timber, such that the electromagnetic radiation is transmitted across the shortest path through the charge of timber. Alternatively, the transmitter and receiver are located in the kiln on opposed sides of the charge of timber, such that the electromagnetic radiation is not transmitted across the shortest path through the charge of timber.

Preferably, the electromagnetic radiation is transmitted substantially transversely across the kiln, in a direction substantially perpendicular to the opposed side walls of the kiln.

Alternatively, the electromagnetic radiation is transmitted at an inclined angle across the kiln, in a direction substantially non-perpendicular to the opposed side walls of the kiln.

The transmitter and the receiver may be located such that a straight line between the transmitter and receiver is through the charge at a non-perpendicular angle to an incident surface of the charge.

The distance travelled by the received electromagnetic radiation is preferably greater than the width of the charge, although the disclosure could be implemented such that the radiation is transmitted through only a section of the charge. On the other hand, the distance travelled by the received electromagnetic radiation may also be greater than twice the width of the charge, particularly where a reflector is used to reflect the transmitted radiation.

Where the transmitter and receiver are located on the same side of the kiln, the method further includes the provision of a reflector and reflecting the electromagnetic radiation from the reflector located on a side of the charge opposed to the transmitter and receiver. The distance travelled by the received electromagnetic radiation is preferably greater than twice the width of the charge.

Preferably, the charge is between 1 and 5 meters in width, and the distance travelled by the received electromagnetic radiation is between 1 and 7 meters, preferably 1.5 to 4 meters, more preferably between about 2.5 and 3.5 meters.

The method is preferably applied when the charge is near its endpoint moisture content. The charge preferably has a moisture content below its fibre saturation point when the method of the disclosure is applied to the charge, more preferably, a moisture content below about 25% and a moisture content above about 7%.

In some circumstances, the method also includes a calibration step including measuring the gain at two different moisture contents and confirming the moisture contents by sampling the charge and oven drying the samples.

In another aspect, there is provided a kiln moisture measurement system for measuring the moisture content of at least part of a charge of timber in a timber drying kiln comprising at least one timber drying chamber, the system including: a transmitter of electromagnetic radiation; a receiver for receiving the electromagnetic radiation; wherein the transmitter and receiver are configured to be on opposed parts of the chamber such that the electromagnetic radiation passes through the at least part of the charge of timber; a controller comprising an electronic processor configured to determine the gain of the electromagnetic radiation by comparing signals indicative of the intensities of the transmitted and received electromagnetic radiation, and further configured to determine a moisture level of the at least part of the charge of timber based on the gain of the electromagnetic radiation.

The transmitter and/or receiver may be mounted on side walls of the chamber.

The transmitter and/or receiver may be mounted on the floor and/or ceiling of the chamber.

The transmitter and/or receiver may be mounted on supports extending from the or a side wall, floor and/or ceiling of the chamber.

In another aspect, there is provided a timber drying kiln comprising the system as herein described.

The kiln may comprise a single chamber configured to dry a charge of timber with the charge of timber in a single position in the chamber.

Alternatively, the kiln may comprise multiple chambers suitable for receiving multiple charges of timber, wherein the or each charge of timber can be moved to each chamber. Preferably, each chamber is configured to deliver different conditions to the or each charge of timber.

Preferably, the kiln comprises one or more pathways along which the charge can be moved through the or each chamber, such as a plurality of pathways configured such that a first charge of timber can be moved along a first pathway in a first direction, and further configured such that a second charge of timber can be moved along a second pathway in a second, opposed direction.

This disclosure may also be said to broadly consist in the parts, elements, and features referred to or indicated herein, individually, or collectively, and any or all combinations of any two or more said parts, elements, or features. Where specific integers are mentioned herein that have known equivalents in the art to which the disclosure relates, such known equivalents are deemed to be incorporated herein as if individually set forth.

BRIEF DESCRIPTION OF THE DRAWINGS

Preferred forms of the disclosure will now be described by way of example only and with reference to the accompanying drawings, in which.

DETAILED DESCRIPTION OF THE DISCLOSURE

The disclosure will be described with reference to a moisture content measuring system in a solid timber heating and/or drying kiln for processing solid timber. It will be appreciated that the disclosure is not intended to be limited only to heating and drying kilns.

The stack of solid timber to be processed is referred to herein as a charge. Charges of timber for drying are usually stacks of sawn timber arranged so as to have a width of between 1.5 and 5 metres, usually between 2.4 and 3.6 meters, and are supported on a carriage or other lumbar charge transporting apparatus or mechanism, so that the charges may be moved efficiently into, through, and out of the kiln. For example, a charge of timber may comprise 20 to 30 layers of 2.4 m or 3.6 m long timber, in which each layer comprises 20 to 30 lengths. Each layer is separated by, for example, hardwood fillets. The Fillets are typically hardwood, softwood, LVL or a metal such as aluminium.

Figure 1:
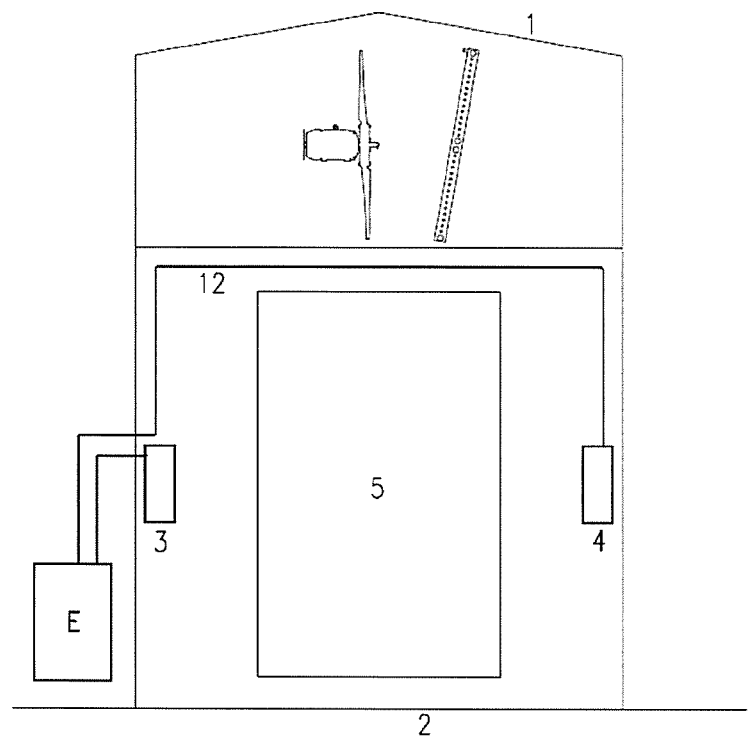
FIG. 1 is a side cross section view of a single path timber drying kiln including an embodiment of the present disclosure.

FIG. 1 shows a preferred example of a moisture measuring system installed in a timber heating and/or drying kiln having a fan and heating means 1 housing a chamber 2 for receiving a charge of timber 5. The length, height and/or width of the chamber 2 may be customised to suit different sites and charges 5 of different sizes and lengths. In an example in accordance with the present disclosure, the kiln 1 has a width of about 5 meters and length of about 40 meters, and the charge 5 has a width of between 1.5 and 5 meters, usually 2.4 meters to 3.6 meters.

Mounted on opposing side walls of the chamber 2 are an antenna being a transmitter for transmitting radio frequency electromagnetic radiation 3 and an antenna being a receiver for receiving the transmitted radio frequency radiation 4.

In this embodiment, the transmitter 3 and receiver 4 are each UHF antenna mounted on the walls of the kiln. Each antenna may comprise, for example, a flat panel antenna, a dipole element backed by a reflector (which may be aluminium) a horn antenna, or any other suitable antenna type. Each antenna may be mounted on the wall, floor or ceiling of the chamber, or on brackets or supports that space each antenna from the wall, floor and/or ceiling.

In some instances the antennae could be free standing rather than directly mounted to the wall.

Figure 6:
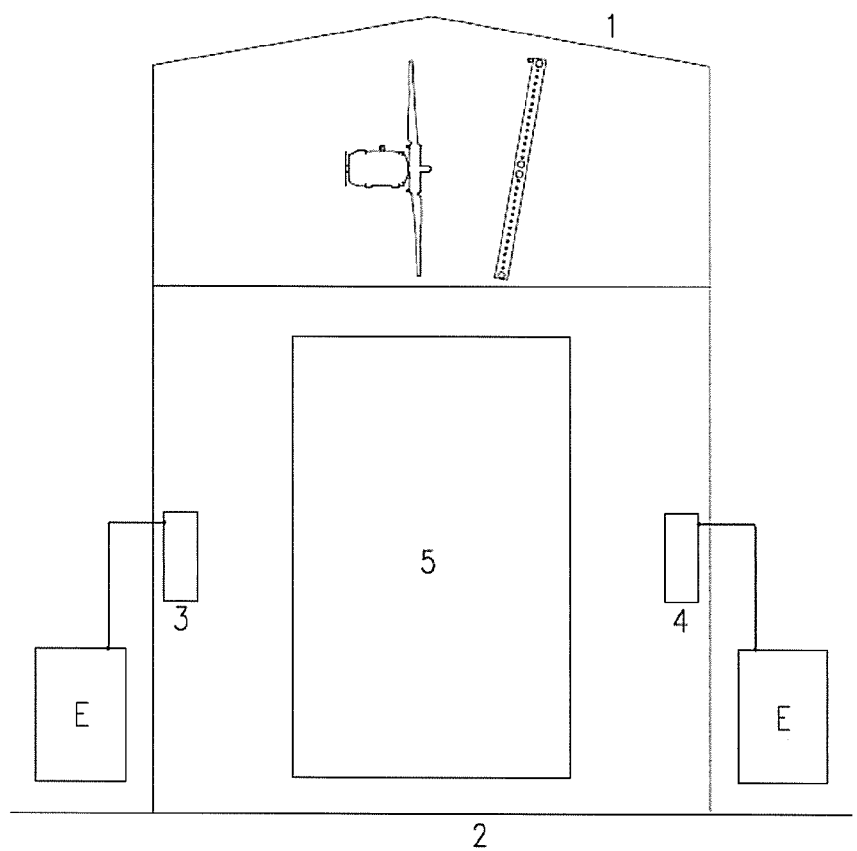
FIG. 6 is a side cross section view of a single path timber drying kiln including alternative embodiments of the present disclosure.

Electronics unit E comprises a controller comprising the electronic equipment and circuitry necessary for generating and transmitting the radiation for the transmitter 3 and receiver 4 respectively, and includes an electronic data processor. For ease of access and protection of sensitive components, unit E is located outside of the chamber 2 and is in communication with the transmitter 3 and receiver 4 via suitably temperature- and humidity-resistant communication cabling/leads 12. In this embodiment, unit E is a single unit. However, as shown in FIG. 6, the components in the unit E may be separated to for example, to situate components more closely to each antenna, 3, 4. Unit E comprises a control circuit 30, as described in more detail with reference to FIG. 13 a or 13b, below. Unit E may comprise a protective outer housing or enclosure, inside which the control circuit 30 is retained.

High-temperature cabling 12 was used to connect the antennae 3, 4 to unit E outside of the chamber 2.

FIGS. 2 to 5 show the transmitter 3 and receiver 4 arranged on the walls in different arrangements.

Figure 2:
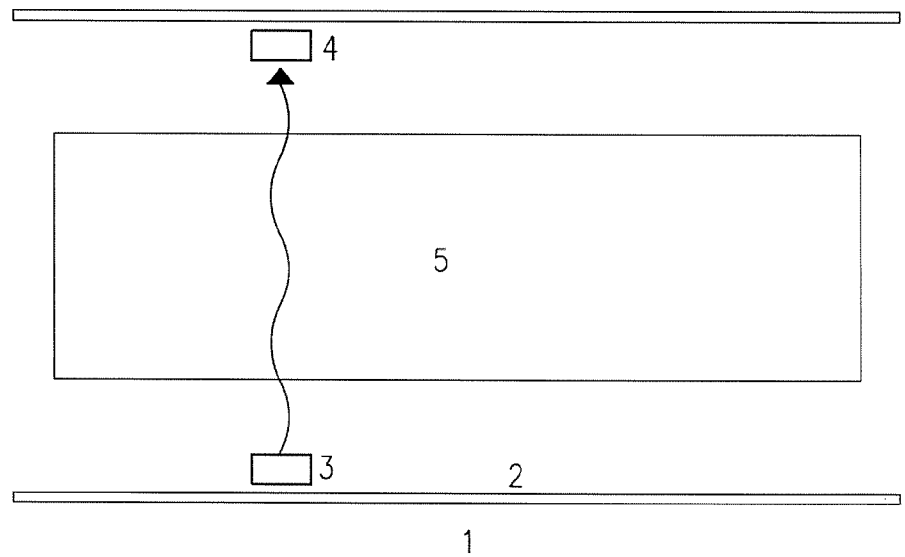
FIGS. 2 to 5 are top plan views of timber drying kilns including alternative embodiments of the present disclosure.

FIG. 2 shows an embodiment wherein the transmitter 3 and receiver 4 are mounted in the chamber 2 such that a straight line between the transmitter 3 and receiver 4 is substantially perpendicular with the side surfaces of the charge 5.

Figure 3:
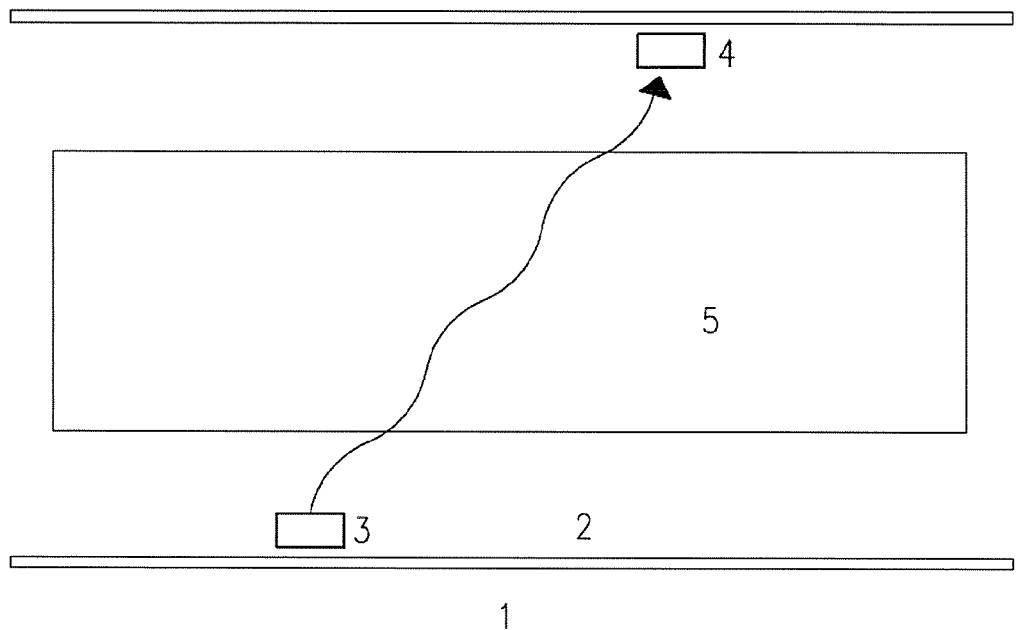

FIG. 3 shows an alternative example of a moisture measuring system, substantially the same as that shown in FIG. 2, wherein the transmitter 3 and receiver 4 are mounted on the walls of the chamber 2 such that a straight line between the transmitter 3 and receiver 4 is non-perpendicular with the side surfaces of the charge 5. It has been found that this arrangement of transmitter 3 and receiver 4 allows the antennae 3, 4 to be separated from each other by a distance of up to 5 meters.

Figure 4:
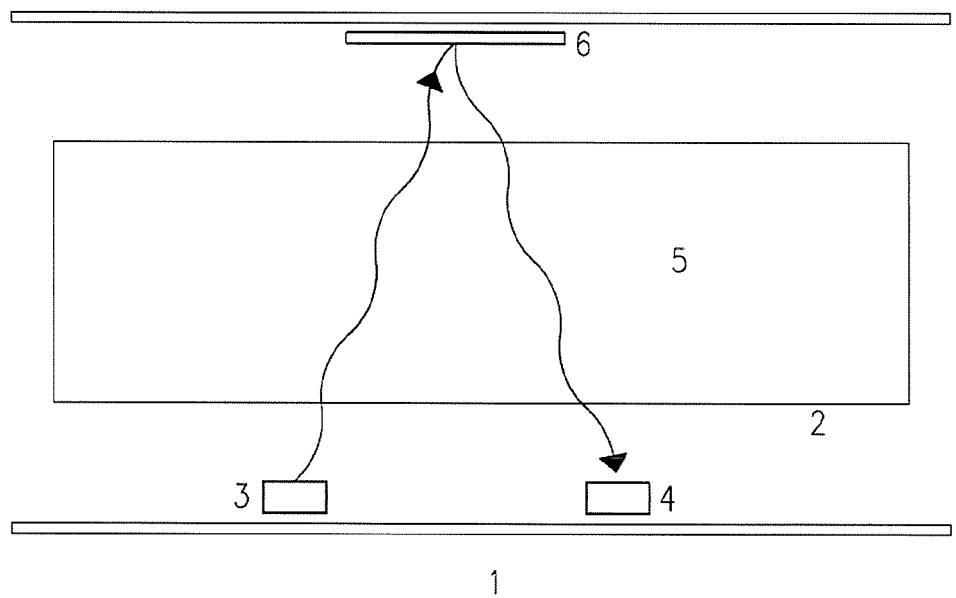
Figure 5:
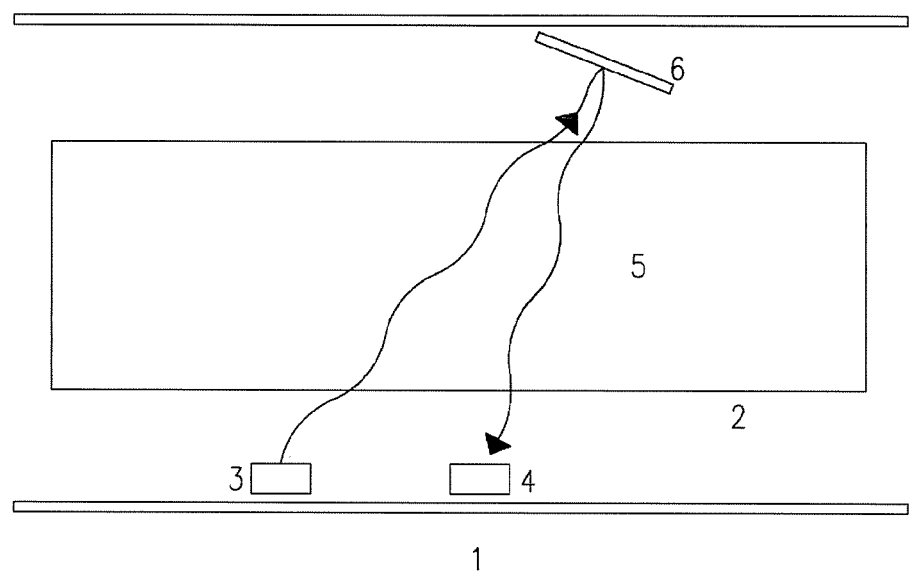

FIGS. 4 and 5 show alternative embodiments where the chamber 2 further comprises a reflector 6 located on one side of the chamber 2 such that the transmitter 3 and receiver 4 may be located on the same other side of the chamber 2, and at least some of the electromagnetic radiation received by the receiver 4 has travelled through the charge 5 twice. The embodiments shown in FIGS. 4 and 5 show the transmitter 3, receiver 4 and reflector 6 arranged such that the electromagnetic radiation received by the receiver 4 has passes through the charge 5 at a non-perpendicular angle. This increases the cross-section of the timber which is sampled by the electromagnetic radiation. Embodiments having the transmitter 3 and receiver 4 on the same side of the chamber 2 are useful in some situations, for example where the kiln is particularly wide, or where the kiln is configured to receive more than one charge 5 at a time, e.g. a double-track kiln. In such kilns, it is more feasible have the transmitter and receiver on one wall, and to place a reflecting body on the opposing side of the charge.

Figure 7:
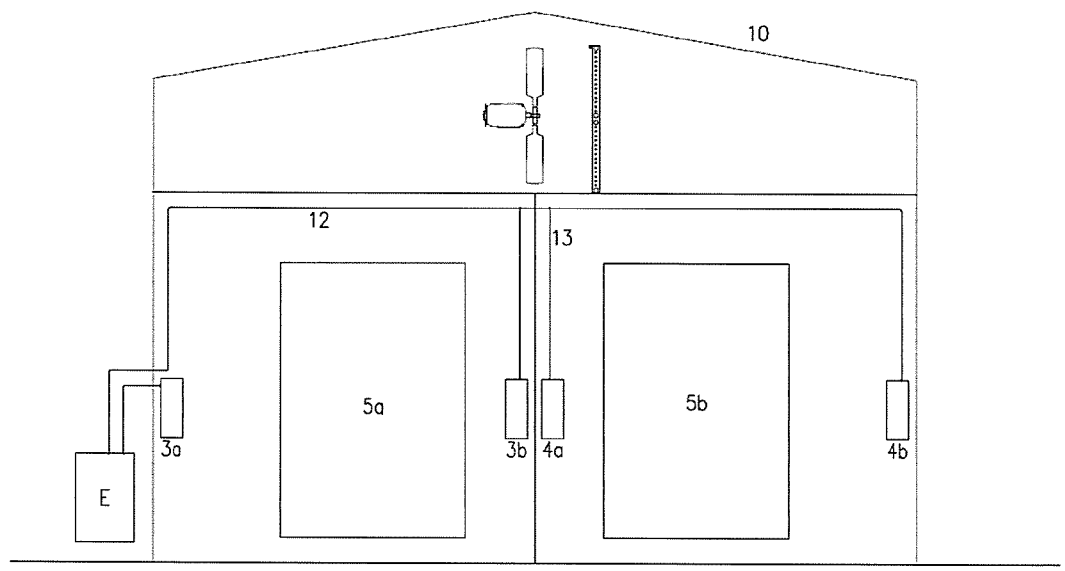
FIG. 7 is a side cross section view of a dual path timber drying kiln including alternative embodiments of the present disclosure.

FIG. 7 shows a double-track kiln having a fan and heating means 10 configured to receive and dry two charges of timber 5a, 5b at the same time. To improve efficiency, double-track kilns 10 may operate continuously, and move charges 5a, 5b through a drying section of the kiln on automatically moving carriages. The charges 5a, 5b may optionally move in opposing directions allowing an outgoing hot dried charge 5a to transfer heat to an area in the vicinity of an incoming cool wet charge 5b at each end of the kiln 10 prior to exiting. In this embodiment, the kiln 10 includes two sets of transmitters 3a, 3b and receivers 4a and 4b.

The centrally located transmitter 3b and centrally located receiver 4a are mounted on supports extending from the floor or ceiling of the kiln 10. To avoid interference with each other, appropriate UHF shielding 13 should be used, or only one set of transmitter and receiver 3a, 4a, 3b, 4b, is used at a time. Interference may also be avoided by the use of different UHF frequencies by each set of transmitter and receiver, effectively the system uses a different signal frequency in each side of the kiln.

Sets of transmitter and receivers may also be switched in sequence, and/or multiplexed signals from sets of transmitter and receivers may be transmitted along a single cable from each side of the kiln to a single controller. The controller may be located between each side of the kiln, but not inside the kiln chambers themselves. The controller may be configured to compensate for any effects on the high temperatures in the kiln on the signal transmitting cable(s). The controller may be configured to apply a compensation or correction factor which compensates for the effects of temperature.

Figure 13A:
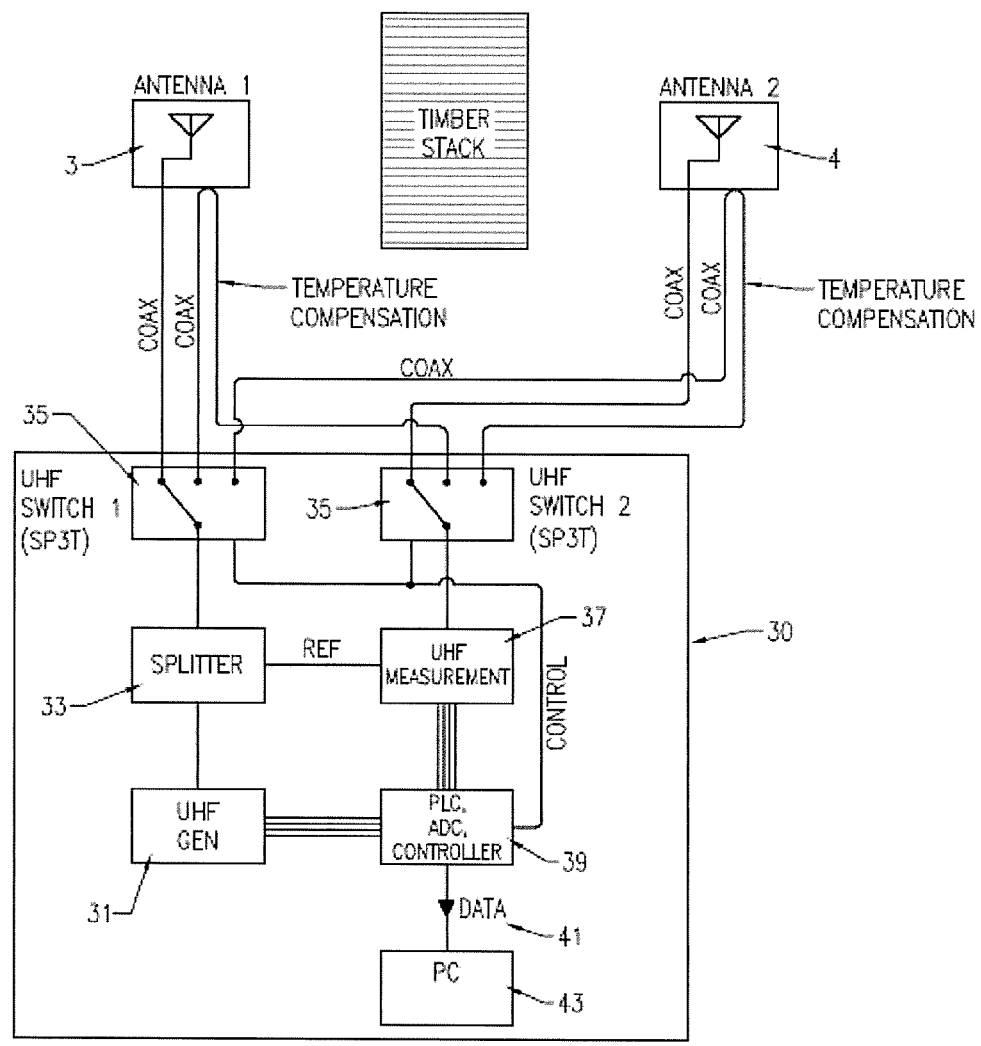
FIGS. 13a and 13b are schematic views of the moisture measurement system of two example embodiments of the present disclosure.
Figure 13B:
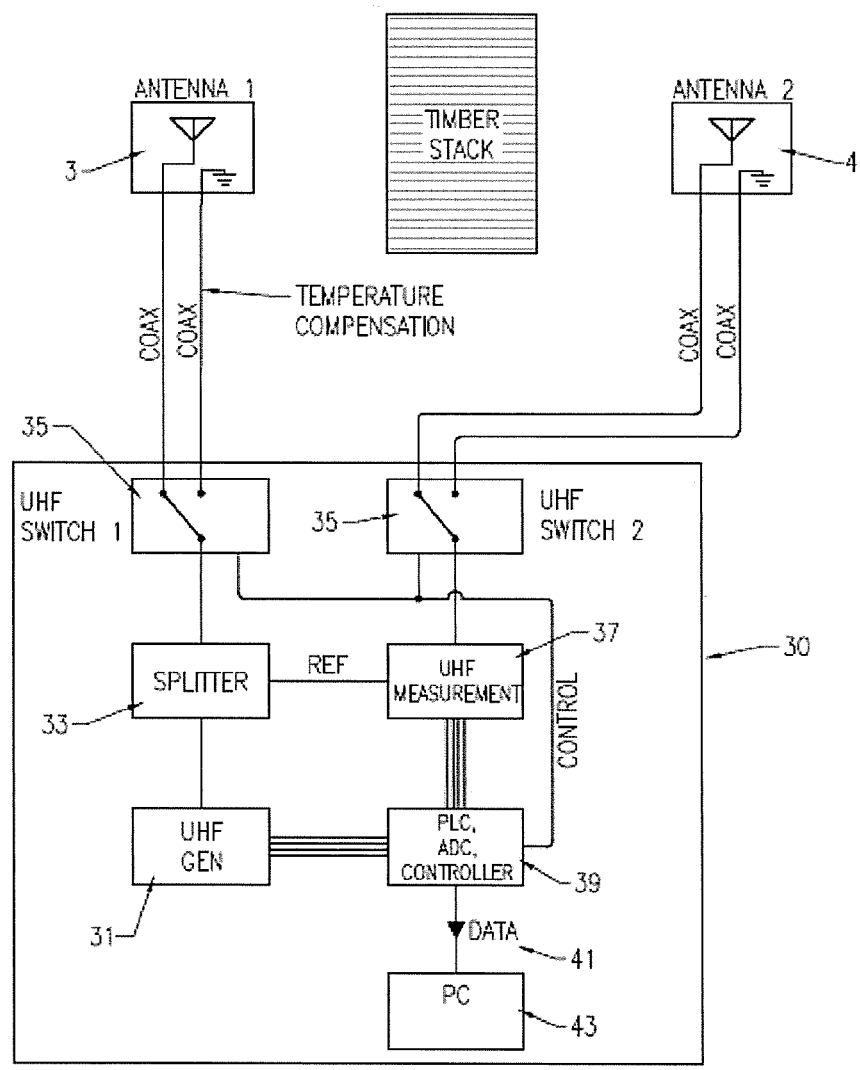
Figure 13C:
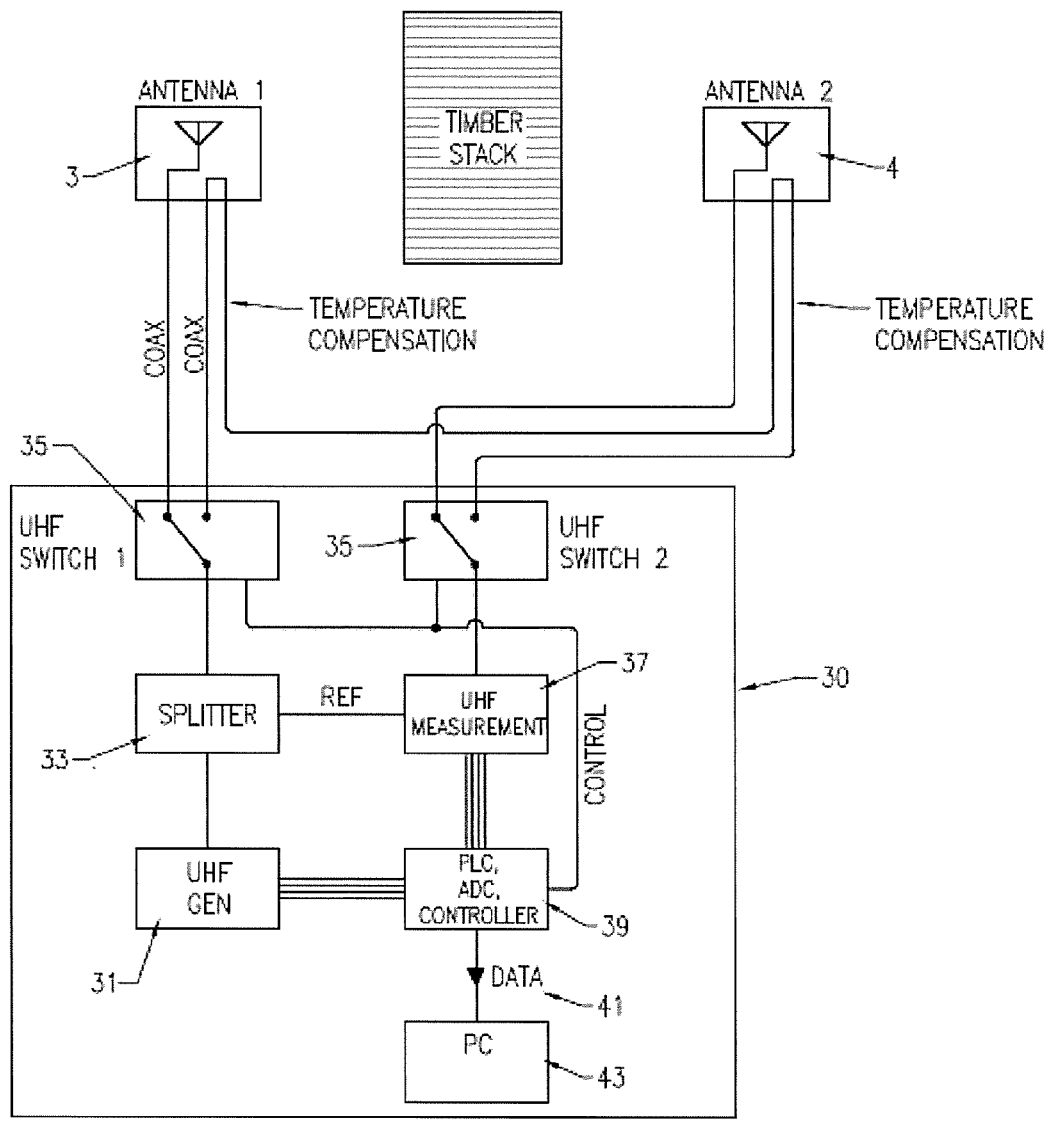
FIG. 13c is a schematic view of the moisture measurement system of a third example embodiment of the present disclosure.

FIG. 13a-c show schematics of different embodiments of the UHF moisture measuring system comprising a transmitting antenna 3, a receiving antenna 4, which form part of a control circuit 30 comprising a UHF generator 31, a splitter 33, two UHF switches 35, a UHF measurement device 37 and a PLC-ADC controller 39 which feeds data 41 to a PC, laptop, tablet or smartphone 43. The control circuit 30 is configured such that a UHF signal can be generated by the UHF generator 31 and selectively sent to either antenna 3, 4 for transmission through the timber stack. The control circuit 30 is further configured to be able to selectively measure the UHF signal received by either antenna 3, 4 and generate an output signal accordingly. The analogue output signal is converted by controller 39 into a digital signal for processing, and/or display by the PC 43. The PC 43 of other electronic processing and display device may be physically connected to circuit 30, or remote from circuit 30. In the latter case a wired or wireless router may be provided to route signals to and from PC 43. The controller 39 receives control signals from the PC 43 for control of the other components of the circuit 30.

The antennae 3, used may have 3 dB power angles of approximately ±60° degrees. In these examples, each antenna is one dipole element backed by an aluminium reflector, and is mounted to the wall of the timber drying kiln. Flat-panel UHF antennae can be used for this application and can be mounted on the walls of the kiln to transmit UHF radio waves through the stack. Antennae 3, 4 can be substantially identical or different. High-temperature cabling 12 is preferably used to connect the antennae 3, 4 to control circuit 30. Control circuit 30 is desirably outside of the chamber 2 so that an operator does not have to enter the chamber 2.

The two antenna 3, 4 are connected to each other and to circuit 30 via suitable cabling, which may be coaxial cabling. Some of the cabling may pass near to, or through the kiln chamber 2 and thus be subject to the relatively high temperatures in the kiln. Consequently, the control circuit 30 is configured to compensate for the effects of these high temperatures on the signals passing through the cables. The control circuit 30 may be configured to generate and apply a temperature compensation factor to the signals transmitted and/or received through the cables.

In the embodiments of FIGS. 13a, 13b, 13c, the temperature compensation may be by way of signal transmission through the cables, whereby sample or reference signals can be transmitted through the circuit 30 and cables, in various different kiln temperature conditions. In the embodiment of FIG. 13b, the temperature compensation may be way of measuring signal reflection between the two antenna 3, 4, in various different kiln conditions, using three pole switches. In the embodiment of FIG. 13c, another temperature compensation arrangement is provided, using two pole switches as per FIG. 13a. The example of FIG. 13c may help to minimise any reflection problems which might impact the temperature compensation calculation.

In all of these examples, a UHF signal is sent to a receiving antenna, mounted somewhere inside the kiln, some distance from the signal generator. Another antenna is mounted on the opposite side of the timber charge and the loss of signal intensity is measured as a change in gain, and provides a signal indicative of the moisture content of the timber charge. However, a change in gain signal can also be caused by a change in the temperature of the signal generating and measuring electronics and the cabling and antennae. This can cause the change in gain signal to be inaccurate. The temperature inside the kiln is known and measured by one or more sensors, and the system can therefore compensate for that known temperature. However, the temperature change of the signal cables is not known. To eliminate any distorting effect of a temperature change in the signal cables, a separate looped cable is run to each antenna, with but not antenna attached. The change in gain is then measured which can only be caused by the temperature of the cabling. This measurement, is used to calculate a temperature compensation factor which is used by the controller.

UHF electromagnetic radiation having a frequency of about 300 MHz (290 MHz to 310 MHz) is directed by the transmitter 3 towards the charge 5. Simulations of the present embodiment showed approximately 95% of the charge 5 interacting with the UHF radiation. It is desirable for the UHF waves to interact with as much timber as possible to get an average moisture content representative of the timber in the charge 5. However, the antennae 3, 4 could be configured to focus the UHF radiation to a width of about 0.5 m in the kiln if a narrower path through the timber stack was desired. A factor to be considered is the size of antenna required. There is only limited space/area that available for use in the middle of a double track kiln. The antenna covers some of the heating surface so cannot be too big. In some instances this may preclude the use of a reflector in the middle of the kiln. For example, embodiments may comprise systems where approximately 90, 80, 70, 60, 50, 30, 20, 10, 5, 2 or 1% of the charge 5 interact with the UHF radiation.

The UHF radiation received by the receiver 4 is compared with the transmitted UHF radiation by the electronic processor 9 of the control system, to generate an output signal indicative of the moisture content of the charge of timber. In this case this comparison is used to determine the gain of the UHF received. Signal gain may be determined according to standard procedures known in the art.

Figure 11:
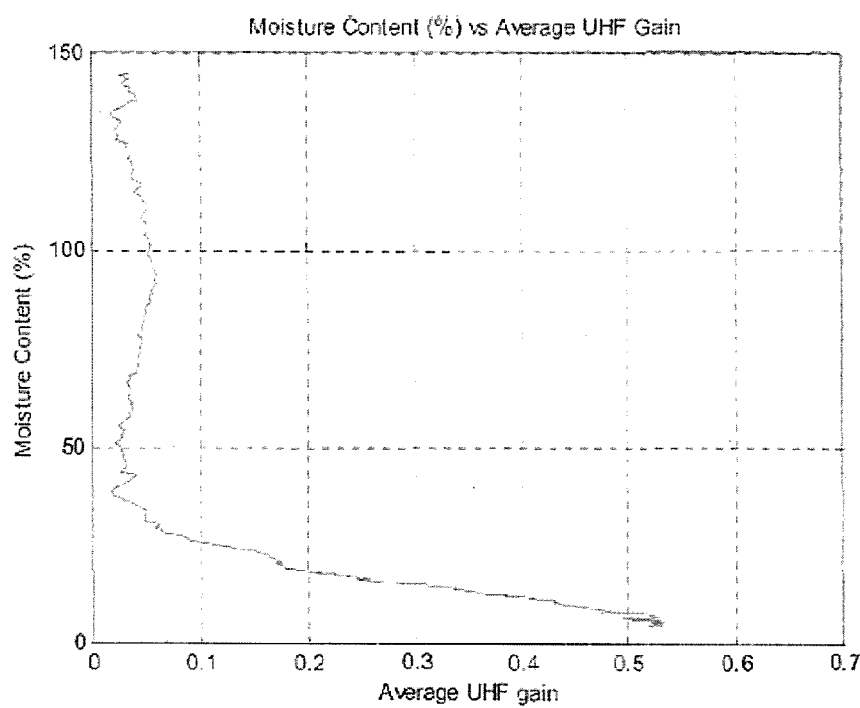
FIG. 11 is a plot of the average measured moisture content of the timber stack versus the UHF gain.
Figure 12:
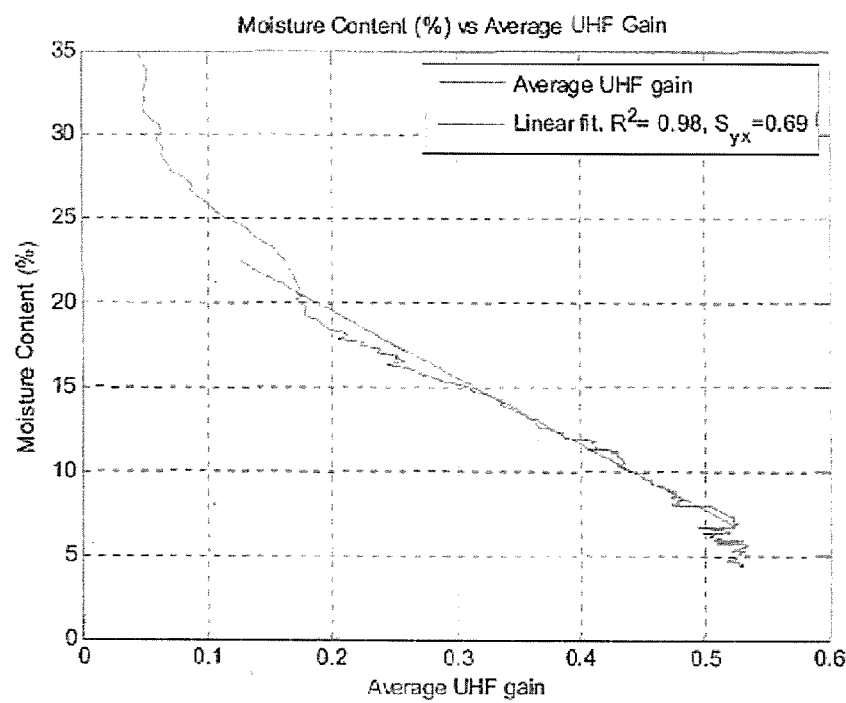
FIG. 12 is an expanded section of the plot shown in FIG. 11, showing the region of moisture content below 30%, and including a line of best fit over a moisture content of 7% to 25%.

UHF signal gain has been found to be more sensitive to changes in moisture content below about the fibre saturation point of the timber in the charge 5, and most sensitive to changes in moisture content between 7% and 30%. The fibre saturation point is the maximum moisture content where all water is bound to the timber cell-walls, and there is a substantial absence of bulk water within cavities in the timber. Within this range there is a linear relationship between average UHF gain and moisture content in the charge 5. Above this range, the UHF signal gain is approximately constant, with a low gain. It is believed that the signal is reflected by the timber and the received signal in this condition is the leakage of the UHF radiation around the sides of the charge 5. Below this range there are fluctuations in the signal. As shown in FIGS. 11 and 12, fitting a line to the endpoint range of moisture content of 8% to 20% gives an $R^2$ of 0.98 and a standard error of 0.33%, indicating that the standard deviation of the final moisture content is about 0.33%.

The problem of measuring moisture content above about 25%/the fibre saturation point may be at least partially addressed by directing the incident UHF radiation at the surface of the charge 5 at a non-perpendicular angle. FIGS. 3 to 5 show alternative embodiments where the transmitter 3, receiver 4 and, optionally, the reflector 6 are configured to provide the incident UHF radiation at non-perpendicular angles.

Calibration of the system may be required between drying operations if the charge size differs. Since the UHF response for a charge 5 is linear within a range of 7%-25%, calibration is achieved by measuring the UHF response at two different moisture contents around the end point and confirming the moisture contents by sampling the charge 5 and oven drying the samples. In broad terms calibration may be achieved by taking the high end and low end measurements and then correcting the slope of the curve between those two points.

Effects in the signal caused by changes in kiln temperature (e.g. cable attenuation, changes in amplitude and/or phase), are accounted for by known methods in the art. In some embodiments, the temperature sensitivity of the cables and other electrical equipment can be ignored for the purposes of moisture content determination as the full implementation of the method can continually estimate the cable attenuation and fully compensate the readings for these.

We have found that the accuracy of the control circuit 30, or parts of it, can be temperature dependent. We therefore also propose implementing temperature control of the control circuit 30, and in particular any circuit enclosure or housing. In one example we control the electronics enclosure temperature to +/−1° C. Such temperature control can be provided by any suitable means such as for example a cooling fan and temperature sensor. More complex or sophisticated temperature control methodology can be used include providing a refrigerated or air conditioned enclosure, a vented enclosure or any other suitable method. The circuit enclosure or housing may be insulated, and may include a heater. The temperature inside the enclosure or housing may be controlled to be higher than the highest ambient temperature in the vicinity, to minimise any need to cool the enclosure or housing.

Further, the spacing of the transmitter and receiver with respect to the part of the kiln on which these components are mounted, and with respect to the timber charge, can be varied to optimise the measurement of moisture in the charge.

We also propose measuring the phase angle between the UHF radiation received by the receiver 4 as compared with the transmitted UHF radiation by the electronic processor 9 of the control system, to generate an output signal. The speed of propagation of an electromagnetic wave is reduced as it passes through the timber charge. As the speed of propagation reduces, so does the wavelength of the wave. This reduction in speed is measurable as a phase change in wave, which is dependent on the density and moisture content of the wood. The phase angle may be determined according to standard procedures known in the art. Measurement of the phase change in the wave transmitted through the timber charge can therefore provide useful information on the moisture content and/or density of the timber charge.

We also propose providing a moisture measuring system which measures moisture of the or each charge of timber at multiple points along the length or width or height of the kiln. For example, the moisture of the charge of timber can be measured at various positions as the charge of timber moves though the kiln. This could be achieved by including multiple moisture measurement systems, at discrete positions along the length of the kiln. In other words, multiple systems as per any of FIGS. 13a to c could be provided at different positions in the kiln.

Figure 13D:
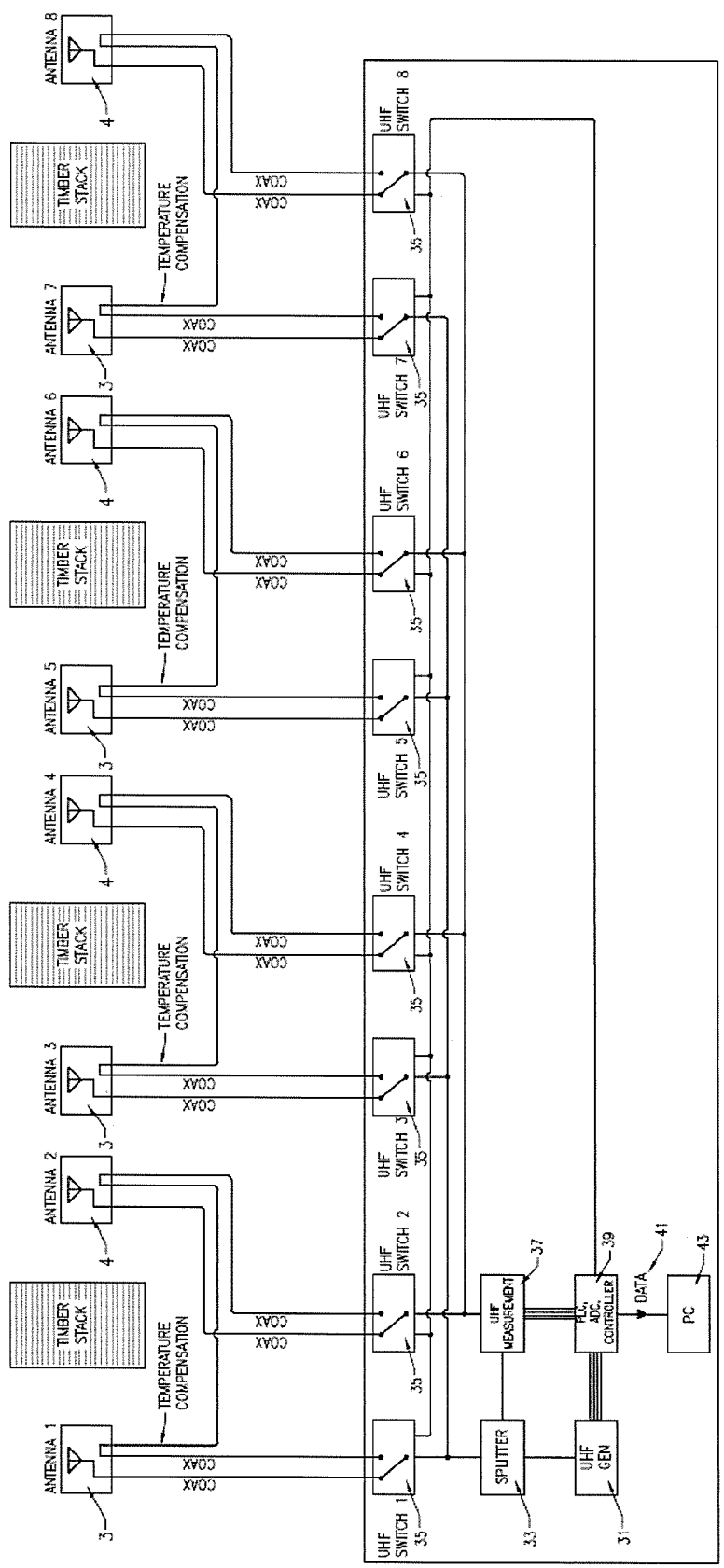
FIG. 13d is a schematic view of the moisture measurement system of a fourth example embodiment of the present disclosure.

However, whilst it is possible to implement temperature control using multiple small enclosures, it may help to reduce costs and complexity to provide only one primary electronics controller with a plurality of UHF switches connecting a plurality of pairs of antennae, for example eight UHF switches connecting four pairs of antennae, of the type shown in FIG. 13d. This will minimise duplication of control components and circuitry, enable a single temperature controlled control enclosure or housing to be used, and will simplify installation.

Example

An automated, computer controlled UHF generator and receiver were used to generate and detect radio waves to determine the UHF transmission over a range of frequencies at regular time intervals as the timber stack was dried. After drying, random samples of the stack were oven dried to determine the average moisture content of the whole kiln stack. The UHF transmission response through the stack was then related to the average moisture content of the boards to determine the viability of using UHF radio waves to measure the stack average moisture content.

Apparatus

A moisture measuring system was installed in a timber drying kiln comprising a transmitting antenna, a receiving antenna and a computer having a controller, signal processor and a UHF signal generator. The antennae used had 3 dB power angles of approximately ±60° degrees. Flat-panel UHF antennas were used for this application and were mounted on the walls of the kiln to transmit UHF radio waves through the stack. Each antenna is one dipole element backed by an aluminium reflector. High-temperature cabling was used to connect the antennae to a measurement system housed in a next-door room.

Method

Figure 10:
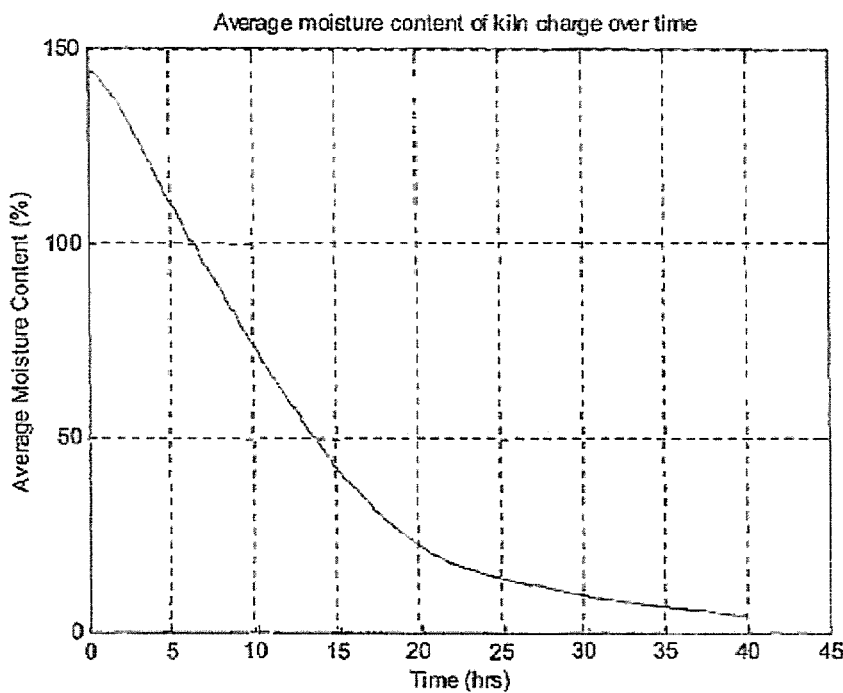
FIG. 10 is a plot of average moisture content of the timber in the kiln charge as determined from continuous weighing of the charge.

In an example method in accordance with aspects of this disclosure, a charge of timber for drying was prepared and put into a kiln for drying using a standard accelerated conventional temperature (ACT) schedule (90° C. dry bulb/60° C. wet bulb). The timber stack was set on loadcells to weigh the stack as it was dried in order to determine moisture content (shown in FIG. 10).

During operation of the kiln, UHF transmission loss through the timber charge in the kiln and the weight of the charge using load cells were recorded. The UHF transmission and gain was measured at frequencies from 250 MHz to 600 MHz in steps of 2 MHz. A plot of average moisture content over time is shown at FIG. 11.

A finite element simulation of the UHF waves interacting with the timber stack showed that, under this configuration of antennae and timber stack size, 95% of the timber charge was interacting with UHF waves (at 300 MHz, and a timber moisture content, moisture content of 10%).

Twenty random samples from the boards were extracted, weighed and oven-dried to determine the moisture content. This was averaged and taken to be the average moisture content of the whole charge at the end of the run.

This moisture content was 5.0% moisture content with a sample standard deviation of 0.8% moisture content and a mean standard deviation of 0.2% moisture content.

The moisture contents thus obtained were compared with the UHF gain.

The UHF gain for each frequency was determined according to standard procedures. Alternatively/additionally, phase angle measurement may provide an additional or different signal output, and may, for example, work at higher moisture contents.

Figure 8:
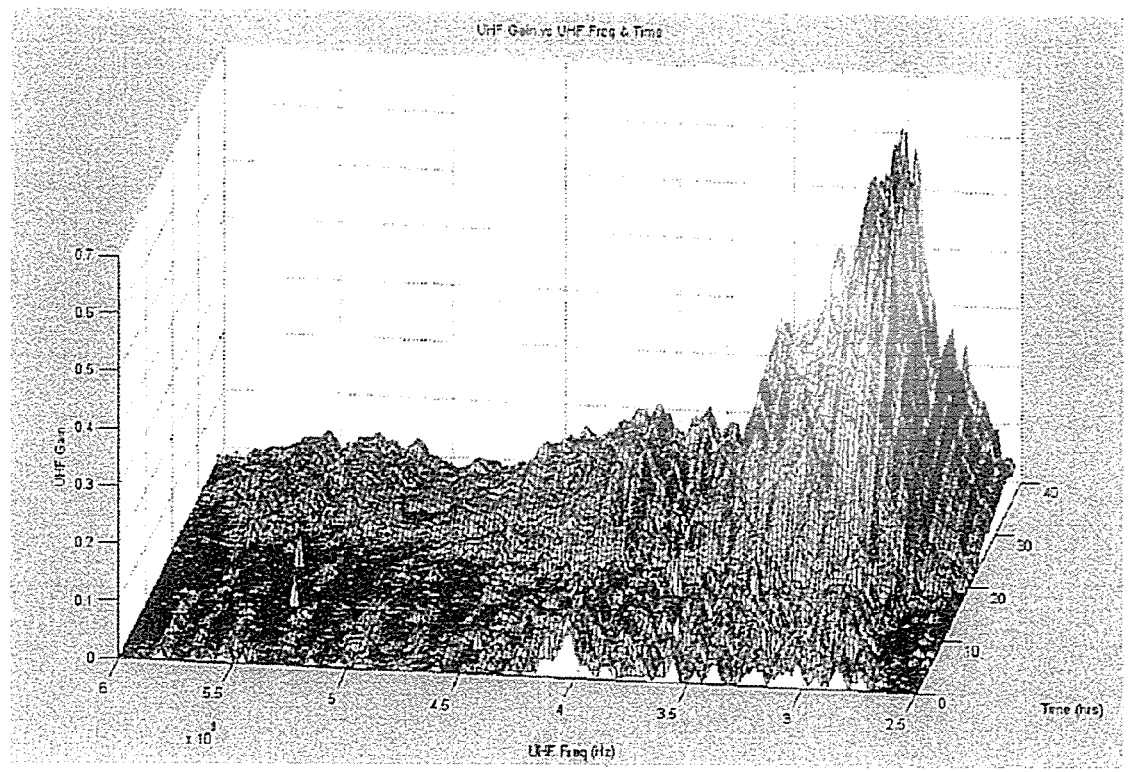
FIG. 8 is a mesh plot of UHF transmission through in-kiln timber stack (100×50 mm) versus frequency and time, according to the particular method described in the Example.
Figure 9:
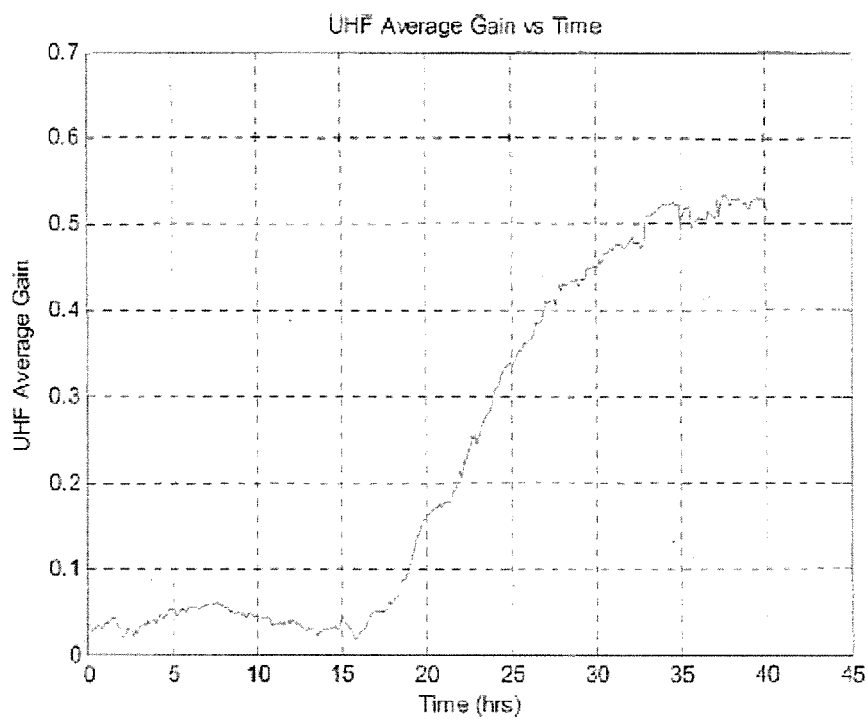
FIG. 9 is a section of the mesh plot of FIG. 8 and shows a plot of average measured UHF transmission gain of the system of the present disclosure over the frequency band 290 MHz to 310 MHz over time.

A mesh plot of the UHF gains for the different frequencies over time (FIG. 8) shows that frequencies below 280 MHz and above 500 MHz were distorted and had interference. and that frequencies between 290 MHz and 310 MHz offered the greatest signal levels. From the mesh plot, a frequency band with the greatest transmission gains was selected (290 MHz to 310 MHz) to produce an average UHF gain which could be related to average timber moisture content in the stack (FIG. 9).

The moisture content plotted against the average UHF transmission gain (FIG. 11) showed that UHF transmission was most sensitive to changes in moisture content below about the fibre saturation point of the timber; above this point the UHF signal gain was approximately constant. Expanding the area where moisture content is below the fibre saturation point (FIG. 12) showed a linear relationship between about 7% and 25% moisture content. Below 7% moisture content there were fluctuations in the signal—without being bound by theory, this could be due to extreme resonances in the timber stack as the moisture content changes. Between moisture content 7 and 25% there is a linear fit to the average UHF gain and produces a standard error of moisture content of 0.7%.

These findings show that it is possible to make antennae which can be mounted in a kiln and can transmit radio frequency electromagnetic radiation, in particular UHF radiation through a stack of drying timber. Therefore, this system is useful in the determination of determining drying of timber, in particular determining a drying end-point of the timber in the kiln.

Variations and modifications to the preferred embodiments of the disclosure described herein will be apparent to those skilled in the art. It is intended that such variations and modifications may be made without departing from the scope of the disclosure and without diminishing its attendant advantages.

Advantages of the Disclosure

Aspects of the present disclosure allows remote, substantially automatic and contact-less moisture measuring of timber charges while the charges are in a drying kiln. Aspects of the disclosure may thus remove the requirement for operators to enter a kiln to attend to moisture measurement, and may also remove the requirement for operators to manually install, manipulate or remove plates in each timber charge, thus improving the safety of the operators.

Further, the large proportion of the charge interacting with the electromagnetic radiation can reduce the likelihood that multiple measurements at multiple locations in a timber charge will be required.

Further, the present disclosure is particularly well suited for progressive and continuous drying kilns, as the moisture measurements of each timber charge can be taken as the charge passes between a transmitter and receiver. It is therefore envisaged that the disclosure encompasses a series of moisture measuring apparatus along a drying kiln such that as a drying charge moves through a kiln the moisture level of the charge can be taken at multiple instances spaced apart along the path of the timber charge through the kiln.

The foregoing advantages described herein are not intended to limit the scope of the disclosure, and further advantages will be apparent to those skilled in the art.

Reference to any prior art in this specification is not, and should not be taken as, an acknowledgement or any form of suggestion that the prior art forms part of the common general knowledge in the field of endeavour in any country in the world.

Where reference is used herein to directional terms such as 'up', 'down', 'forward', 'rearward', 'horizontal', 'vertical' etc., those terms refer to when the apparatus is in a typical in-use position, and are used to show and/or describe relative directions or orientations.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to".

The terms "approximately," "about," and "substantially" as used herein represent an amount close to the stated amount that still performs a desired function or achieves a desired result. For example, in some embodiments, as the context may permit, the terms "approximately", "about", and "substantially" may refer to an amount that is within less than or equal to 10% of, within less than or equal to 5% of, and within less than or equal to 1% of the stated amount.

Reference to any prior art in this specification is not, and should not be taken as, an acknowledgement or any form of suggestion that that prior art forms part of the common general knowledge in the field of endeavour in any country in the world.

The disclosed apparatus and systems may also be said broadly to consist in the parts, elements and features referred to or indicated in the specification of the application, individually or collectively, in any or all combinations of two or more of said parts, elements or features.

Where, in the foregoing description reference has been made to integers or components having known equivalents thereof, those integers are herein incorporated as if individually set forth.

Depending on the embodiment, certain acts, events, or functions of any of the algorithms, methods, or processes described herein can be performed in a different sequence, can be added, merged, or left out altogether (for example, not all described acts or events are necessary for the practice of the algorithms). Moreover, in certain embodiments, acts or events can be performed concurrently, for example, through multi-threaded processing, interrupt processing, or multiple processors or processor cores or on other parallel architectures, rather than sequentially.

It should be noted that various changes and modifications to the presently preferred embodiments described herein will be apparent to those skilled in the art. Such changes and modifications may be made without departing from the spirit and scope of the disclosed apparatus and systems and without diminishing its attendant advantages. For instance, various components may be repositioned as desired. It is therefore intended that such changes and modifications be included within the scope of the disclosed apparatus and systems. Moreover, not all of the features, aspects and advantages are necessarily required to practice the disclosed apparatus and systems. Accordingly, the scope of the disclosed apparatus and systems is intended to be defined only by the claims that follow.

The invention claimed is:

1. A method for measuring the moisture level of a charge of timber in a timber drying kiln, including steps of:
   (a) providing a timber drying kiln, wherein the kiln comprises:
      i. a transmitter configured to transmit electromagnetic radiation; and
      ii. a receiver configured to receive electromagnetic radiation;
      wherein the transmitter and receiver are configured such that the electromagnetic radiation transmitted from the transmitter passes through at least a part of the charge of timber, and is received by the receiver;
   (b) transmitting electromagnetic radiation from the transmitter; wherein the transmitted electromagnetic radiation has a first intensity;
   (c) receiving the transmitted electromagnetic radiation at the receiver; wherein the received electromagnetic radiation has a second intensity;
   (d) determining, using an electronic data processor, a property of the electromagnetic radiation by comparing the first intensity of the electromagnetic radiation transmitted from the transmitter to the second intensity of the electromagnetic radiation received by the receiver; wherein the property is gain, phase angle, or phase difference of the electromagnetic radiation;
   (e) determining a moisture level of the charge based on the determined property of the electromagnetic radiation;
   wherein the method is a kiln moisture measurement method.

2. The method of claim 1, wherein the charge of timber has primary dimension, and the transmitter and receiver are located such that the received electromagnetic radiation is transmitted through the primary dimension of the charge.

3. The method of claim 1, wherein the primary dimension is the width, length or height of the charge of timber.

4. The method of any one of the preceding claims, wherein the electromagnetic radiation has a frequency in the range of 150 MHz to 4 GHz.

5. The method of any one of the preceding claims 1 to 3, wherein the electromagnetic radiation has a frequency in the VHF or UHF bands, that is, between 150 MHz and 1 GHz.

6. The method of any one of the preceding claims 1 to 3, wherein the electromagnetic radiation has a frequency in the range of about 280 MHz to 500 MHz.

7. The method of any one of the preceding claims 1 to 3, wherein the electromagnetic radiation has a frequency in the range of about 290 MHz to about 310 MHz.

8. The method of any one of the preceding claims 1 to 3, wherein the transmitter and receiver are located on opposed side walls of the kiln.

9. The method of any one of claims 1 to 3, wherein the transmitter and/or receiver are mounted on supports extending from the or a side wall, floor or ceiling of the chamber.

10. The method of claim 8, wherein the transmitter and receiver are located in the kiln on opposed sides of the charge of timber, such that the electromagnetic radiation is transmitted across the shortest path through the charge of timber.

11. The method of claim 8, wherein the transmitter and receiver are located in the kiln on opposed sides of the charge of timber, such that the electromagnetic radiation is not transmitted across the shortest path through the charge of timber.

12. The method of claim 8, wherein the electromagnetic radiation is transmitted substantially transversely across the kiln, in a direction substantially perpendicular to the opposed side walls of the kiln.

13. The method of claim 8, wherein the electromagnetic radiation is transmitted at an inclined angle across the kiln, in a direction substantially non-perpendicular to the opposed side walls of the kiln.

14. The method of any one of the preceding claims 1 to 3, wherein the transmitter and the receiver are located such that a straight line between the transmitter and receiver is through the charge at a non-perpendicular angle to an incident surface of the charge.

15. The method of any one of the preceding claims 1 to 3, wherein the distance travelled by the electromagnetic radiation between the transmitter and receiver is greater than the width of the charge.

16. The method of any one of claims 1 to 3, wherein the transmitter and receiver are located on the same side of the kiln, and the method further includes steps of providing a reflector and reflecting the electromagnetic radiation from the reflector located on a side of the charge opposed to the transmitter and receiver.

17. The method of claim 16, wherein the distance travelled by the received electromagnetic radiation is greater than twice the width of the charge.

18. The method of any one of the preceding claims 1 to 3, wherein the width of the charge is between 1 and 5 meters.

19. The method of any one of the preceding claims 1 to 3, wherein the distance travelled by the received electromagnetic radiation is between 1 and 7 meters.

20. The method of any one of the preceding claims 1 to 3, wherein the distance travelled by the received electromagnetic radiation is about 5 meters.

21. The method of any one of the preceding claims 1 to 3, wherein the charge has a moisture content below its fibre saturation point.

22. The method of any one of the preceding claims 1 to 3, wherein the charge has a moisture content below about 25%.

23. The method of any one of the preceding claims 1 to 3, wherein the charge has a moisture content above about 7%.

24. The method of any one of the preceding claims 1 to 3, further comprising a calibration step including measuring the gain at two different moisture contents and confirming the moisture contents by sampling the charge and oven drying the samples.

25. The method of any one of the preceding claims 1 to 3, comprising determining, using an electronic data processor, the gain of the electromagnetic radiation by comparing the intensities of the transmitted and received electromagnetic radiation; and
determining a moisture level of the charge based on the gain of the electromagnetic radiation.

26. The method of any one of the preceding claims 1 to 3, comprising determining, using an electronic data processor, the phase angle or phase difference of the electromagnetic radiation.

27. A kiln moisture measurement system for measuring the moisture content of at least part of a charge of timber in a timber drying kiln comprising at least one timber drying chamber, the system including
a transmitter of electromagnetic radiation having a first intensity;
a receiver for receiving the electromagnetic radiation that is transmitted from the transmitter, wherein the received electromagnetic radiation has a second intensity;
wherein the transmitter and receiver are configured such that the electromagnetic radiation passes through the at least part of the charge of timber;
a controller comprising an electronic processor configured to determine a property of the electromagnetic radiation by comparing signals indicative of intensities of the transmitted first intensity and the received second intensity electromagnetic radiation, and further configured to determine a moisture level of the at least part of the charge of timber based on the determined property of the electromagnetic radiation;
wherein the property is gain, phase angle, or phase difference of the electromagnetic radiation.

28. The system of claim 27, wherein the charge has a primary dimension, and the transmitter and receiver are located such that the received electromagnetic radiation transmits through the primary dimension of the charge.

29. The system of claim 28, wherein the primary dimension is the width, length or height of the charge of timber.

30. The system of any one of claims 27 to 29, wherein the wherein the electromagnetic radiation has a frequency in the range of 150 MHz to 4 GHz.

31. The system of any one of claims 27 to 29, wherein the electromagnetic radiation has a frequency in the VHF or UHF bands, that is, between 150 MHz and 1 GHz.

32. The system of any one of claims 27 to 29, wherein the electromagnetic radiation has a frequency in the range of about 280 MHz to 500 MHz.

33. The system of any one of claims 27 to 29, wherein the electromagnetic radiation has a frequency in the range of about 290 MHz to about 310 MHz.

34. The system of any one of claims 27 to 29, wherein the transmitter and receiver are located on opposed side walls of the chamber of the kiln.

35. The system of any one of claims 27 to 29, wherein the transmitter and/or receiver are mounted on supports extending from the or a side wall, floor or ceiling of the chamber.

36. The method of claim 34, wherein the transmitter and receiver are located in the chamber such that the electromagnetic radiation is transmitted across the shortest path through the charge of timber.

37. The method of claim 34, wherein the transmitter and receiver are located in the chamber, such that the electromagnetic radiation is not transmitted across the shortest path through the charge of timber.

38. The method of claim 34, wherein the electromagnetic radiation is transmitted substantially transversely across the chamber, in a direction substantially perpendicular to the opposed side walls of the chamber.

39. The method of claim 34, wherein the electromagnetic radiation is transmitted at an inclined angle across the chamber, in a direction substantially non-perpendicular to the opposed side walls of the chamber.

40. The system of any one of claims 27 to 29, wherein the transmitter and the receiver are located in the chamber such that a straight line between the transmitter and receiver is through the charge and at a non-perpendicular angle to an incident surface of the charge.

41. The system of any one of claims 27 to 29, wherein the transmitter and receiver are located such that the distance travelled by the received electromagnetic radiation through the charge is greater than the width of the charge.

42. The system of any one of claims 27 to 29, wherein the transmitter and receiver are arranged in the chamber such that the charge is moved between the transmitter and receiver.

43. The system of any one of claims 27 to 29, wherein the transmitter and receiver are located on the same side of the chamber, and the system further includes a reflector located on an opposing part of the chamber and configured to reflect the electromagnetic radiation from the transmitter to the receiver.

44. The system of claim 43, wherein the transmitter, receiver and reflector are arranged in the chamber such that the charge is moved between the reflector on one side, and the transmitter and receiver on the other side.

45. The system of claim 43, wherein the transmitter, receiver and reflector are located such that the distance travelled by the received electromagnetic radiation is greater than twice the width of the charge.

46. The system of claim 43, wherein the distance travelled by the received electromagnetic radiation is between 1 and 7 meters.

47. The system of any one of claims 27 to 29, wherein the distance travelled by the received electromagnetic radiation is about 5 meters.

48. The system of any one of claims 27 to 29, wherein the width of the charge is between 1.5 and 5 meters.

49. The system of any one of claims 27 to 29, wherein the charge has a moisture content below its fibre saturation point.

50. The system of any one of claims 27 to 29, wherein the charge has a moisture content below about 25%.

51. The system of any one of claims 27 to 29, wherein the charge has a moisture content above about 7%.

52. The system of any one of claims 27 to 29, wherein the transmitter and/or receiver are mounted on side walls of the chamber.

53. The system of any one of claims 27 to 29, wherein the controller is temperature controlled.

54. The system of claim 53 wherein the controller is provided in an enclosure or housing, the enclosure or housing being temperature controlled.

55. The system of any one of claims 27 to 29, further comprising a calibration step including measuring the gain at two different moisture contents and confirming the moisture contents by sampling the charge and oven drying the samples.

56. The system of any one of claims 27 to 29, comprising determining, using an electronic data processor, the gain of the electromagnetic radiation by comparing the intensities of the transmitted and received electromagnetic radiation; and
   determining a moisture level of the charge based on the gain of the electromagnetic radiation.

57. The system of any one of claims 27 to 29, comprising determining, using an electronic data processor, the phase angle or phase difference of the electromagnetic radiation.

58. The system of any one of claims 27 to 29, wherein the transmitter and the receiver are each an antenna, wherein each antenna is independently selected from: a flat panel antenna, a dipole element backed by a reflector, or a horn antenna.

59. A timber drying kiln comprising the system of any one of claims 27 to 29.

60. The kiln of claim 59 comprising a single chamber configured to dry a charge of timber with the charge of timber in a single position in the chamber.

61. The kiln of claim 59 comprising multiple chambers, wherein the or each charge of timber can be moved to each chamber.

62. The kiln of claim 61 wherein each chamber is configured to deliver different conditions to the or each charge of timber.

63. The kiln of claim 59 wherein the kiln comprises one or more pathways along which the charge can be moved through the or each chamber.

64. The kiln of claim 63 comprising a plurality of pathways, configured such that a first charge of timber can be moved along a first pathway in a first direction, and further configured such that a second charge of timber can be moved along a second pathway in a second, opposed direction.

* * * * *